(12) United States Patent
Chillemi et al.

(10) Patent No.: US 6,921,749 B1
(45) Date of Patent: Jul. 26, 2005

(54) POLYPEPTIDES DERIVED FROM ENDOSTATIN EXHIBITING ANTIANGIOGENIC ACTIVITY

(75) Inventors: Francesco Chillemi, Milan (IT); Pierangelo Francescato, Milan (IT); Marina Ziche, Florence (IT)

(73) Assignees: Universita' Degli Studi di Milano, Milan (IT); Universita' Degli Studi di Firenze, Florence (IT)

( * ) Notice: Subject to any disclaimer, the term of this patent is extended or adjusted under 35 U.S.C. 154(b) by 0 days.

(21) Appl. No.: 09/958,489

(22) PCT Filed: Apr. 11, 2000

(86) PCT No.: PCT/EP00/03236

§ 371 (c)(1),
(2), (4) Date: Feb. 19, 2002

(87) PCT Pub. No.: WO00/63249

PCT Pub. Date: Oct. 26, 2000

(30) Foreign Application Priority Data

Apr. 15, 1999 (IT) .......................................... MI99A0777

(51) Int. Cl.[7] .............................................. A61K 38/00
(52) U.S. Cl. ............................. 514/12; 514/2; 530/300; 530/324
(58) Field of Search ....................... 514/2, 12; 530/300, 530/324

(56) References Cited

U.S. PATENT DOCUMENTS 6,342,219 B1 * 1/2002 Thorpe et al. ........... 424/145.1
6,630,448 B2 * 10/2003 O'Reilly et al. .............. 514/12

FOREIGN PATENT DOCUMENTS

| WO | WO 97/15666 | 5/1997 |
| WO | WO 99/29855 | 6/1999 |
| WO | WO 99/48924 | 9/1999 |

* cited by examiner

*Primary Examiner*—Christopher Tate
*Assistant Examiner*—Roy Teller
(74) *Attorney, Agent, or Firm*—Young & Thompson

(57) ABSTRACT

Polypeptides with sequence corresponding or homologous to that of endostatin, having inhibiting activity on angiogenesis, are useful in the treatment of angiogenesis-dependent tumors.

7 Claims, 3 Drawing Sheets

SEQUENCE LISTING

<160> NUMBER OF SEQ ID NOS: 8

<210> SEQ ID NO 1
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (33)
<223> OTHER INFORMATION: Cys(tBu)

<400> SEQUENCE: 1

His Thr His Gln Asp Phe Gln Pro Val Leu His Leu Val Ala Leu Asn
 1               5                  10                  15

Thr Pro Leu Ser Gly Gly Met Arg Gly Ile Arg Gly Ala Asp Phe Gln
            20                  25                  30

Cys Phe Gln Gln Ala Arg Ala
        35

<210> SEQ ID NO 2
<211> LENGTH: 50
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

Val Gly Leu Ser Gly Thr Phe Arg Ala Phe Leu Ser Ser Arg Leu Gln
 1               5                  10                  15

Asp Leu Tyr Ser Ile Val Arg Arg Ala Asp Arg Gly Ser Val Pro Ile
            20                  25                  30

Val Asn Leu Lys Asp Glu Val Leu Ser Pro Ser Trp Asp Ser Leu Phe
            35                  40                  45

Ser Gly
    50

<210> SEQ ID NO 3
<211> LENGTH: 45
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 3

Ser Gln Gly Gln Val Gln Pro Gly Ala Arg Ile Phe Ser Phe Asp Gly
 1               5                  10                  15

Arg Asp Val Leu Arg His Pro Ala Trp Pro Gln Lys Ser Val Trp His
            20                  25                  30

Gly Ser Asp Pro Ser Gly Arg Arg Leu Met Glu Ser Tyr
            35                  40                  45

<210> SEQ ID NO 4
<211> LENGTH: 50
<212> TYPE: PRT
<213> ORGANISM: Artificial Sequence
<220> FEATURE:
<223> OTHER INFORMATION: Description of Artificial Sequence: Synthetic
      polypeptide -continued

```
<220> FEATURE:
<221> NAME/KEY: MOD_RES
<222> LOCATION: (39)
<223> OTHER INFORMATION: Cys(tBu)

<400> SEQUENCE: 4

Cys Glu Thr Trp Arg Thr Glu Thr Thr Gly Ala Thr Gly Gln Ala Ser
 1               5                  10                  15

Ser Leu Leu Ser Gly Arg Leu Leu Glu Gln Lys Ala Ala Ser Cys His
            20                  25                  30

Asn Ser Tyr Ile Val Leu Cys Ile Glu Asn Ser Phe Met Thr Ser Phe
        35                  40                  45

Ser Lys
    50

<210> SEQ ID NO 5
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)
<223> OTHER INFORMATION: His(Trt)
<220> FEATURE:
<221> NAME/KEY: MOD_RES
<222> LOCATION: (2)
<223> OTHER INFORMATION: Thr(tBu)
<220> FEATURE:
<221> NAME/KEY: MOD_RES
<222> LOCATION: (3)
<223> OTHER INFORMATION: His(Trt)
<220> FEATURE:
<221> NAME/KEY: MOD_RES
<222> LOCATION: (5)
<223> OTHER INFORMATION: Asp(OtBu)
<220> FEATURE:
<221> NAME/KEY: MOD_RES
<222> LOCATION: (11)
<223> OTHER INFORMATION: His(Trt)
<220> FEATURE:
<221> NAME/KEY: MOD_RES
<222> LOCATION: (17)
<223> OTHER INFORMATION: Thr(tBu)
<220> FEATURE:
<221> NAME/KEY: MOD_RES
<222> LOCATION: (20)
<223> OTHER INFORMATION: Ser(tBu)
<220> FEATURE:
<221> NAME/KEY: MOD_RES
<222> LOCATION: (24)
<223> OTHER INFORMATION: Arg(Pbf)
<220> FEATURE:
<221> NAME/KEY: MOD_RES
<222> LOCATION: (27)
<223> OTHER INFORMATION: Arg(Pbf)
<220> FEATURE:
<221> NAME/KEY: MOD_RES
<222> LOCATION: (30)
<223> OTHER INFORMATION: Asp(OtBu)
<220> FEATURE:
<221> NAME/KEY: MOD_RES
<222> LOCATION: (33)
<223> OTHER INFORMATION: Cys(tBu)
<220> FEATURE:
<221> NAME/KEY: MOD_RES
<222> LOCATION: (38)
<223> OTHER INFORMATION: Arg(Pbf)

<400> SEQUENCE: 5

His Thr His Gln Asp Phe Gln Pro Val Leu His Leu Val Ala Leu Asn
```

```
                 1               5              10              15
Thr Pro Leu Ser Gly Gly Met Arg Gly Ile Arg Gly Ala Asp Phe Gln
               20                        25                30

Cys Phe Gln Gln Ala Arg Ala
           35

<210> SEQ ID NO 6
<211> LENGTH: 50
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (4)
<223> OTHER INFORMATION: Ser(tBu)
<220> FEATURE:
<221> NAME/KEY: MOD_RES
<222> LOCATION: (6)
<223> OTHER INFORMATION: Thr(tBu)
<220> FEATURE:
<221> NAME/KEY: MOD_RES
<222> LOCATION: (8)
<223> OTHER INFORMATION: Arg(Pbf)
<220> FEATURE:
<221> NAME/KEY: MOD_RES
<222> LOCATION: (12)
<223> OTHER INFORMATION: Ser(tBu)
<220> FEATURE:
<221> NAME/KEY: MOD_RES
<222> LOCATION: (13)
<223> OTHER INFORMATION: Ser(tBu)
<220> FEATURE:
<221> NAME/KEY: MOD_RES
<222> LOCATION: (14)
<223> OTHER INFORMATION: Arg(Pbf)
<220> FEATURE:
<221> NAME/KEY: MOD_RES
<222> LOCATION: (17)
<223> OTHER INFORMATION: Asp(OtBu)
<220> FEATURE:
<221> NAME/KEY: MOD_RES
<222> LOCATION: (19)
<223> OTHER INFORMATION: Tyr(tBu)
<220> FEATURE:
<221> NAME/KEY: MOD_RES
<222> LOCATION: (20)
<223> OTHER INFORMATION: Ser(tBu)
<220> FEATURE:
<221> NAME/KEY: MOD_RES
<222> LOCATION: (23)
<223> OTHER INFORMATION: Arg(Pbf)
<220> FEATURE:
<221> NAME/KEY: MOD_RES
<222> LOCATION: (24)
<223> OTHER INFORMATION: Arg(Pbf)
<220> FEATURE:
<221> NAME/KEY: MOD_RES
<222> LOCATION: (26)
<223> OTHER INFORMATION: Asp(OtBu)
<220> FEATURE:
<221> NAME/KEY: MOD_RES
<222> LOCATION: (27)
<223> OTHER INFORMATION: Arg(Pbf)
<220> FEATURE:
<221> NAME/KEY: MOD_RES
<222> LOCATION: (29)
<223> OTHER INFORMATION: Ser(tBu)
<220> FEATURE:
<221> NAME/KEY: MOD_RES
<222> LOCATION: (36)
<223> OTHER INFORMATION: Lys(Boc)
<220> FEATURE:
<221> NAME/KEY: MOD_RES
<222> LOCATION: (37)
```

```
<223> OTHER INFORMATION: Asp(OtBu)
<220> FEATURE:
<221> NAME/KEY: MOD_RES
<222> LOCATION: (38)
<223> OTHER INFORMATION: Glu(OtBu)
<220> FEATURE:
<221> NAME/KEY: MOD_RES
<222> LOCATION: (41)
<223> OTHER INFORMATION: Ser(tBu)
<220> FEATURE:
<221> NAME/KEY: MOD_RES
<222> LOCATION: (43)
<223> OTHER INFORMATION: Ser(tBu)
<220> FEATURE:
<221> NAME/KEY: MOD_RES
<222> LOCATION: (44)
<223> OTHER INFORMATION: Trp(Boc)
<220> FEATURE:
<221> NAME/KEY: MOD_RES
<222> LOCATION: (45)
<223> OTHER INFORMATION: Asp(OtBu)
<220> FEATURE:
<221> NAME/KEY: MOD_RES
<222> LOCATION: (46)
<223> OTHER INFORMATION: Ser(tBu)
<220> FEATURE:
<221> NAME/KEY: MOD_RES
<222> LOCATION: (49)
<223> OTHER INFORMATION: Ser(tBu)

<400> SEQUENCE: 6

Val Gly Leu Ser Gly Thr Phe Arg Ala Phe Leu Ser Ser Arg Leu Gln
 1               5                  10                  15

Asp Leu Tyr Ser Ile Val Arg Arg Ala Asp Arg Gly Ser Val Pro Ile
             20                  25                  30

Val Asn Leu Lys Asp Glu Val Leu Ser Pro Ser Trp Asp Ser Leu Phe
         35                  40                  45

Ser Gly
     50

<210> SEQ ID NO 7
<211> LENGTH: 45
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)
<223> OTHER INFORMATION: Ser(tBu)
<220> FEATURE:
<221> NAME/KEY: MOD_RES
<222> LOCATION: (10)
<223> OTHER INFORMATION: Arg(Pbf)
<220> FEATURE:
<221> NAME/KEY: MOD_RES
<222> LOCATION: (13)
<223> OTHER INFORMATION: Ser(tBu)
<220> FEATURE:
<221> NAME/KEY: MOD_RES
<222> LOCATION: (15)
<223> OTHER INFORMATION: Asp(OtBu)
<220> FEATURE:
<221> NAME/KEY: MOD_RES
<222> LOCATION: (17)
<223> OTHER INFORMATION: Arg(Pbf)
<220> FEATURE:
<221> NAME/KEY: MOD_RES
<222> LOCATION: (18)
<223> OTHER INFORMATION: Asp(OtBu)
<220> FEATURE:
<221> NAME/KEY: MOD_RES
<222> LOCATION: (21)
```

```
<223> OTHER INFORMATION: Arg(Pbf)
<220> FEATURE:
<221> NAME/KEY: MOD_RES
<222> LOCATION: (22)
<223> OTHER INFORMATION: His(Trt)
<220> FEATURE:
<221> NAME/KEY: MOD_RES
<222> LOCATION: (25)
<223> OTHER INFORMATION: Trp(Boc)
<220> FEATURE:
<221> NAME/KEY: MOD_RES
<222> LOCATION: (28)
<223> OTHER INFORMATION: Lys(Boc)
<220> FEATURE:
<221> NAME/KEY: MOD_RES
<222> LOCATION: (29)
<223> OTHER INFORMATION: Ser(tBu)
<220> FEATURE:
<221> NAME/KEY: MOD_RES
<222> LOCATION: (31)
<223> OTHER INFORMATION: Trp(Boc)
<220> FEATURE:
<221> NAME/KEY: MOD_RES
<222> LOCATION: (32)
<223> OTHER INFORMATION: His(Trt)
<220> FEATURE:
<221> NAME/KEY: MOD_RES
<222> LOCATION: (34)
<223> OTHER INFORMATION: Ser(tBu)
<220> FEATURE:
<221> NAME/KEY: MOD_RES
<222> LOCATION: (35)
<223> OTHER INFORMATION: Asp(OtBu)
<220> FEATURE:
<221> NAME/KEY: MOD_RES
<222> LOCATION: (37)
<223> OTHER INFORMATION: Ser(tBu)
<220> FEATURE:
<221> NAME/KEY: MOD_RES
<222> LOCATION: (39)
<223> OTHER INFORMATION: Arg(Pbf)
<220> FEATURE:
<221> NAME/KEY: MOD_RES
<222> LOCATION: (40)
<223> OTHER INFORMATION: Arg(Pbf)
<220> FEATURE:
<221> NAME/KEY: MOD_RES
<222> LOCATION: (43)
<223> OTHER INFORMATION: Glu(OtBu)
<220> FEATURE:
<221> NAME/KEY: MOD_RES
<222> LOCATION: (44)
<223> OTHER INFORMATION: Ser(tBu)
<220> FEATURE:
<221> NAME/KEY: MOD_RES
<222> LOCATION: (45)
<223> OTHER INFORMATION: Tyr(tBu)

<400> SEQUENCE: 7

Ser Gln Gly Gln Val Gln Pro Gly Ala Arg Ile Phe Ser Phe Asp Gly
 1               5                  10                  15

Arg Asp Val Leu Arg His Pro Ala Trp Pro Gln Lys Ser Val Trp His
            20                  25                  30

Gly Ser Asp Pro Ser Gly Arg Arg Leu Met Glu Ser Tyr
        35                  40                  45

<210> SEQ ID NO 8
<211> LENGTH: 50
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
```

```
<222> LOCATION: (1)
<223> OTHER INFORMATION: Cys(Trt)
<220> FEATURE:
<221> NAME/KEY: MOD_RES
<222> LOCATION: (2)
<223> OTHER INFORMATION: Glu(OtBu)
<220> FEATURE:
<221> NAME/KEY: MOD_RES
<222> LOCATION: (3)
<223> OTHER INFORMATION: Thr(tBu)
<220> FEATURE:
<221> NAME/KEY: MOD_RES
<222> LOCATION: (4)
<223> OTHER INFORMATION: Trp(Boc)
<220> FEATURE:
<221> NAME/KEY: MOD_RES
<222> LOCATION: (5)
<223> OTHER INFORMATION: Arg(Pbf)
<220> FEATURE:
<221> NAME/KEY: MOD_RES
<222> LOCATION: (6)
<223> OTHER INFORMATION: Thr(tBu)
<220> FEATURE:
<221> NAME/KEY: MOD_RES
<222> LOCATION: (7)
<223> OTHER INFORMATION: Glu(OtBu)
<220> FEATURE:
<221> NAME/KEY: MOD_RES
<222> LOCATION: (8)
<223> OTHER INFORMATION: Thr(tBu)
<220> FEATURE:
<221> NAME/KEY: MOD_RES
<222> LOCATION: (9)
<223> OTHER INFORMATION: Thr(tBu)
<220> FEATURE:
<221> NAME/KEY: MOD_RES
<222> LOCATION: (12)
<223> OTHER INFORMATION: Thr(tBu)
<220> FEATURE:
<221> NAME/KEY: MOD_RES
<222> LOCATION: (16)
<223> OTHER INFORMATION: Ser(tBu)
<220> FEATURE:
<221> NAME/KEY: MOD_RES
<222> LOCATION: (17)
<223> OTHER INFORMATION: Ser(tBu)
<220> FEATURE:
<221> NAME/KEY: MOD_RES
<222> LOCATION: (20)
<223> OTHER INFORMATION: Ser(tBu)
<220> FEATURE:
<221> NAME/KEY: MOD_RES
<222> LOCATION: (22)
<223> OTHER INFORMATION: Arg(Pbf)
<220> FEATURE:
<221> NAME/KEY: MOD_RES
<222> LOCATION: (25)
<223> OTHER INFORMATION: Glu(OtBu)
<220> FEATURE:
<221> NAME/KEY: MOD_RES
<222> LOCATION: (27)
<223> OTHER INFORMATION: Lys(Boc)
<220> FEATURE:
<221> NAME/KEY: MOD_RES
<222> LOCATION: (30)
<223> OTHER INFORMATION: Ser(tBu)
<220> FEATURE:
<221> NAME/KEY: MOD_RES
<222> LOCATION: (31)
<223> OTHER INFORMATION: Cys(Trt)
<220> FEATURE:
<221> NAME/KEY: MOD_RES
<222> LOCATION: (32)
<223> OTHER INFORMATION: His(Trt)
<220> FEATURE:
<221> NAME/KEY: MOD_RES
<222> LOCATION: (34)
<223> OTHER INFORMATION: Ser(tBu)
<220> FEATURE:
```

```
<221> NAME/KEY: MOD_RES
<222> LOCATION: (35)
<223> OTHER INFORMATION: Tyr(tBu)
<220> FEATURE:
<221> NAME/KEY: MOD_RES
<222> LOCATION: (39)
<223> OTHER INFORMATION: Cys(tBu)
<220> FEATURE:
<221> NAME/KEY: MOD_RES
<222> LOCATION: (41)
<223> OTHER INFORMATION: Glu(OtBu)
<220> FEATURE:
<221> NAME/KEY: MOD_RES
<222> LOCATION: (43)
<223> OTHER INFORMATION: Ser(tBu)
<220> FEATURE:
<221> NAME/KEY: MOD_RES
<222> LOCATION: (46)
<223> OTHER INFORMATION: Thr(tBu)
<220> FEATURE:
<221> NAME/KEY: MOD_RES
<222> LOCATION: (47)
<223> OTHER INFORMATION: Ser(tBu)
<220> FEATURE:
<221> NAME/KEY: MOD_RES
<222> LOCATION: (49)
<223> OTHER INFORMATION: Ser(tBu)
<220> FEATURE:
<221> NAME/KEY: MOD_RES
<222> LOCATION: (50)
<223> OTHER INFORMATION: Lys(Boc)

<400> SEQUENCE: 8

Cys Glu Thr Trp Arg Thr Glu Thr Thr Gly Ala Thr Gly Gln Ala Ser
 1               5                  10                  15

Ser Leu Leu Ser Gly Arg Leu Leu Glu Gln Lys Ala Ala Ser Cys His
            20                  25                  30

Asn Ser Tyr Ile Val Leu Cys Ile Glu Asn Ser Phe Met Thr Ser Phe
        35                  40                  45

Ser Lys
    50
```

POLYPEPTIDES DERIVED FROM ENDOSTATIN EXHIBITING ANTIANGIOGENIC ACTIVITY

The present invention relates to polypeptides with antiangiogenic activity.

TECHNOLOGICAL BACKGROUND

Angiogenesis, the outgrowth of new capillaries from pre-existing vessels, is essential for physiological and pathological conditions including tumor growth and metastasis (1–3). Angiogenesis is a complex multistep process that includes proliferation, migration and differentiation of endothelial cells, degradation of extracellular matrix, microtubule formation and sprouting of new capillary branches (3,4)

Endostatin is a 22 kDa C-terminal fragment of collagen XVIII that specifically inhibits endothelial proliferation in vitro and potently inhibits angiogenesis and tumor growth in vivo (5). Systemic administration of non refolded precipitated protein expressed in E. coli caused growth regression of experimental tumors in mice (5,6). We reported that human full-length endostatin produced by E. coli expression system is able to block fibroblast growth factor-2 (FGF-2) and vascular endothelial growth factor (VEGF) induced proliferation and migration of microvascular endothelial cells (7).

The production of large amount of endostatin can be difficult. Thus the availability of smaller molecule with sequence homology with endostatin endowed with biological activity can be useful.

The present invention relates to polypeptides comprising ten to sixty amino acid residues with a sequence corresponding or homologous to that or endostatin, having angiogenesis-inhibiting activity, useful for the treatment of angiogenesis-dependent tumours.

The present invention also relates to a process for the preparation of said polypeptides.

The invention further relates to pharmaceutical formulations containing one or more of said polypeptides.

Endostatin is a protein having antiangiogenic activity, isolated by J. Folkman and M. O'Reilly (EP 0 857 210).

Examples of the polypeptides prepared according to the invention are the following.
(I) nonatriacontapeptide: His-Thr-His-Gln-Asp-Phe-Gln-Pro-Val-Leu-His-Leu-Val-Ala-Leu-Asn-Thr-Pro-Leu-Ser-Gly-Gly-Met-Arg-Gly-Ile-Arg-Gly-Ala-Asp-Phe-Gln-Cys(tBu)-Phe-Gln-Gln-Ala-Arg-Ala (SEQ ID NO: 1)
(II) pentacontapeptide: Val-Gly-Leu-Ser-Gly-Thr-Phe-Arg-Ala-Phe-Leu-Ser-Ser-Arg-Leu-Gln-Asp-Leu-Tyr-Ser-Ile-Val-Arg-Arg-Ala-Asp-Arg-Gly-Ser-Val-Pro-Ile-Val-Asn-Leu-Lys-Asp-Glu-Val-Leu-Ser-Pro-Ser-Trp-Asp-Ser-Leu-Phe-Ser-Gly (SEQ ID NO: 2)
(III) pentatetracontapeptide: Ser-Gln-Gly-Gln-Val-Gln-Pro-Gly-Ala-Arg-Ile-Phe-Ser-Phe-Asp-Gly-Arg-Asp-Val-Leu-Arg-His-Pro-Ala-Trp-Pro-Gln-Lys-Ser-Val-Trp-His-Gly-Ser-Asp-Pro-Ser-Gly-Arg-Arg-Leu-Met-Glu-Ser-Tyr (SEQ ID NO: 3)
(IV) pentacontapeptide: Cys-Glu-Thr-Trp-Arg-Thr-Glu-Thr-Thr-Gly-Ala-Thr-Gly-Gln-Ala-Ser-Ser-Leu-Leu-Ser-Gly-Arg-Leu-Leu-Glu-Gln-Lys-Ala-Ala-Ser-Cys-His-Asn-Ser-Tyr-Ile-Val-Leu-Cys(tBu)-Ile-Glu-Asn-Ser-Phe-Met-Thr-Ser-Phe-Ser-Lys (SEQ ID NO: 4).

These polypeptides have remarkable antiangiogenic activity in the in vitro inhibition test on endothelial cells proliferation and migration (16). More particularly, non-atriacontapeptide I turned out to be equipotential to endostatin.

The process for the preparation of the polypeptides of the invention is based on the following general methods and reactions used in peptide synthesis.

Amino groups of the amino acids can be protected by use of the 9-fluorenylmethoxycarbonyl (Fmoc), tert-butoxycarbonyl (Boc), benzyloxycarbonyl (Z), trityl (Trt) groups and other groups commonly used in peptide chemistry.

The carboxylic group can be protected by means of the tert-butyl ester, benzyl ester, p-methoxybenzyl ester and others conventionally used for said purposes.

These protective groups, as it will be illustrated in is detail in the examples, can be removed according to processes known in literature, such as by treatment with trifluoroacetic acid, anhydrous hydrofluoric acid, piperidine and the like, according to circumstances.

The amino acids can be condensed by using active esters such as pentafluorophenyl ester (OPfp), 3-hydroxy-4-oxo-3,4-dihydro-1,2,3-benzothiazine ester (ODhbT), or carboxy-activators such as benzotriazol-1-yl-oxy-tris-pyrrolidino-phosphonium hexafluorophosphate (PyBop), 2-(1H-benzotriazol-1-yl-1,1,3,3-tetramethyl)-uronium tetrafluoroborate (TBTU) and the other activators conventionally used for this type of reactions.

The purification of the polypeptides described in the present invention can also be carried out according to known techniques of protein chemistry, such as reverse phase HPLC, gel filtration, ion exchange chromatography and preparative electro-phoresis.

For example, the process of the present invention can be carried out as follows, using the solid phase peptide synthesis and the automatic synthesizer Biolynx plus, mod. 4170 by Novabiochem (Nottingham, Great Britain) (17).

The protection of the α-amino groups in the amino acids is carried out by use of 9-fluorenylmethoxycarbonyl (Fmoc). The functional groups of the amino acids side chains are protected using the following protective groups: tert-butyl for aspartic acid, glutamic acid, serine, threonine and tyrosine; tert-butoxycarbonyl for lysine and trypthophan; trityl for histidine; 2,2,4,6,7-pentamethyl-dihydro-benzofuran-5-sulfonyl for arginine; tert-butyl for cysteine of polypeptide I and for the third cysteine of polypeptide IV; trityl for the two other cysteines of polypeptide IV.

The synthesis is gradually carried out starting from the C-terminal Fmoc-amino acid, attached to a resin by an ester bond, consisting of polyethyleneoxide grafted to a polystyrene matrix and functionalized by a 4-hydroxymethyl-phenoxyacetic acid residue (18). Fmoc is removed by using a solution of piperidine in dimethylformamide (DMF). Pentafluorophenyl esters of Fmoc-amino acids are generally used for the condensation reactions. In the case of serine and threonine, the use of ODhbt esters was preferred, whereas in the case of arginine and histidine the carboxylic group was activated by PyBop in the presence of diisopropylethylamine, with three hour reaction times. To maximize the reaction yields, a five equivalent excess of Fmoc-amino acid is used. The times of deprotection and condensation reactions are automatically determined by the synthesizer; the technician will select the acylation times only in the case of activation with PyBop.

The peptide is cleaved from the resin, at the same time removing all the protective groups, by acidolysis with trifluoroacetic acid in the presence of 5% anisole and 1% ethanedithiol.

The resulting crude polypeptides are purified by reverse phase semipreparative HPLC, using a column (250×10 mm) filled with Source TM 15 RPC (Pharmacia Biotech AB, Uppsala, Sweden). Polypeptides are eluted with a linear gradient from 0% to 60% of acetonitrile in 0.1% aqueous TFA, at a 5 ml/min flow rate with detection at 226 nm; 10–15 mg of product are loaded for each run.

The main fractions are collected and freeze-dried.

The purified polypeptides are characterized by amino acid analysis and electrospray mass spectrometry with a Finnigan Mat apparatus mod. LCQ.

The present invention also relates to the pharmaceutical compositions comprising the polypeptides of the invention or a non toxic salt thereof, in mixture with a suitable diluent or carrier.

The following examples further illustrate the invention without limiting it.

EXAMPLE 1

His(Trt)-Thr(tBu)-His-(Trt)-Gln-Asp(OtBu)-Phe-Gln-Pro-Val-Leu-His(Trt)-Leu-Val-Ala-Leu-Asn-Thr(tBu)-Pro-Leu-Ser(tBu)-Gly-Gly-Met-Arg(Pbf)-Gly-Ile-Arg(Pbf)-Gly-Ala-Asp(OtBu)-Phe-Gln-Cys(tBu)-Phe-Gln-Gln-Ala-Arg(Pbf)-Ala-resin (SEQ ID NO: 5).

500 mg (0.1 moles) of Fmoc-Ala-resin were suspended in 20 ml of DMF and after 2 hours they were loaded into the reaction column.

The Pmoc-amino acid-resin was then subjected to the following treatments: a) washings with DMF; b) removal of Fmoc by treatment with a 20% piperidine solution in DMF; c) washings with DMF; d) condensation with the suitable Fmoc-amino acid active ester (5 equivalents) in the presence of N-hydroxy-benzotriazole (5 equivalents) as catalyst, with the addition of an anionic dye (Novachrome, Calbiochem-Novabiochem AG, Laufelfingen, Switzerland) for automatically monitoring the reaction time.

The carboxyl was activated by using PyBop, without addition of dye, only in the case of Fmoc-Arg(Pbf) and Fmoc-His(Trt).

This cycle of operations was repeated thirty-eight times with the suitable Fmoc-amino acid to finally obtain the protected resin-nonatriacontapeptide. The product was then placed in a sintered glass funnel and washed in succession with DMF, tert-amyl alcohol, acetic acid, tert-amyl alcohol, methylene chloride and ethyl ether. After drying under vacuum, 760 mg of protected resin-nonatriacontapeptide were obtained.

EXAMPLE 2

His-Thr-His-Gln-Asp-Phe-Gln-Pro-Val-Leu-His-Leu-Val-Ala-Leu-Asn-Thr-Pro-Leu-Ser-Gly-Gly-Met-Arg-Gly-Ile-Arg-Gly-Ala-Asp-Phe-Gln-Cys(tBu)-Phe-Gln-Gln-Ala-Arg-Ala (nonatriacontapeptide I) (SEQ ID NO: 1).

760 mg of protected resin-nonatriacontapeptide were suspended in 141 ml of TFA and added with 7.5 ml of anisole and 1.5 ml of ethanedithiol and the mixture was reacted for 2 hours with occasional stirring. After filtration under vacuum, the resin was washed with TPA (2×50 ml). The filtrate was added with dry ethyl ether to precipitate the polypeptide. The product was filtered, repeatedly washed with dry ethyl ether and finally dried under vacuum over KOH.

Nonatriacontapeptide I was purified by semipreparative EPLC as described above, to obtain 195 mg of pure nonatriacontapeptide. [α] −43.0°(c=0.5, water). Mass spectrum: molecular peak (M+1)=4376 Da. Amino acid analysis: Asp= 3.1(3); Thr=1.98(2); Ser=0.99(1); Glu=5.2(5); Pro=1.8(2); Gly=3.95(4); Ala=3.98(4); Cys=1.1(1); Val=1.97(2); Met= 0.96(1); Ile=1.2(2); Leu 4.2(4); Phe=2.98(3); His=3.1(3); Arg=2.96(3).

EXAMPLE 3

Val-Gly-Leu-Ser(tBu)-Gly-Thr(tBu)-Phe-Arg(Pbf)-Ala-Phe-Leu-Ser(tBu)-Ser(tBu)-Arg(Pbf)-Leu-Gln-Asp(OtBu)-Leu-Tyr(tBu)-Ser(tBu)-Ile-Val-Arg(Pbf)-Arg(Pbf)-Ala-Asp(OtBu)-Arg(Pbf)-Gly-Ser(tBu)-Val-Pro-Ile-Val-Asn-Leu-Lys(Boc)-Asp(OtBu)-Glu(OtBu)-Val-Leu-Ser(tBu)-Pro-Ser(tBu)-Trp(Boc)-Asp(OtBu)-Ser(tBu)-Leu-Phe-Ser(tBu)-Gly-resin. (SEQ ID NO: 6)

770 mg (0.1 mmoles) of Fmoc-Gly-resin were suspended in 30 ml of DMF and after two hours were loaded into the reaction column. The operations described in example 1 were then repeated for forty-nine times, using the suitable Fmoc-amino acid in each run.

In this synthesis also, the Fmoc-Arg(Pbf) and Fmoc-His (Trt) carboxylic groups were activated with PyBop, those of Fmoc-Ser(tBu) and Fmoc-Thr(tBu) with Dhbt ester, whereas for all the other Fmoc-amino acids the Pfp ester was used. After assembling all of the amino acids, the product was washed as described in example 1, and dried under vacuum. 1200 mg of protected resin-pentacontapeptide were obtained.

EXAMPLE 4

Val-Gly-Leu-Ser-Gly-Thr-Phe-Arg-Ala-Phe-Leu-Ser-Ser-Arg-Leu-Gln-Asp-Leu-Tyr-Ser-Ile-Val-Arg-Arg-Ala-Asp-Arg-Gly-Ser-Val-Pro-Ile-Val-Asn-Leu-Lys-Asp-Glu-Val-Leu-Ser-Pro-Ser-Trp-Asp-Ser-Leu-Phe-Ser-Gly (pentacontapeptide II) (SEQ ID NO: 2).

1200 mg of protected resin-pentacontapeptide were treated with 188 ml of TFA, 10 ml of anisole and 2 ml of ethanedithiol. Then the procedure described in example 2 was followed. 140 mg of pure pentacontapeptide were obtained.

[α] −12.5°(c=0.04, water). Mass spectrum: molecular peak (M+1)=5514 Da. Amino acid analysis: Asp=4.89(5); Thr=1.02(1); Ser=8.91(9); Glu=1.97(2); Pro=2.1(2); Gly= 3.91(4); Ala=1.97(2); Val=4.88(5); Ile=2.0(2); Leu=6.87(7); Tyr=1.11(1); Phe=3.2(3); Lys=0.97(1); Arg=4.88(5); Trp= 0.96(1).

EXAMPLE 5

Ser(tBu)-Gln-Gly-Gln-Val-Gln-Pro-Gly-Ala-Arg(Pbf)-Ile-Phe-Ser(tBu)-Phe-Asp(OtBu)-Gly-Arg(Pbf)-Asp(OtBu)-Val-Leu-Arg(Pbf)-His(Trt)-Pro-Ala-Trp(Boc)-Pro-Gln-Lys (Boc)-Ser(tBu)-Val-Trp(Boc)-His(Trt)-Gly-Ser(tBu)-Asp (OtBu)-Pro-Ser(tBu)-Gly-Arg(Pbf)-Arg(Pbf)-Leu-Met-Glu (OtBu)-Ser(tBu)-Tyr(tBu)-resin (SEQ ID NO: 7).

555 mg (0.1 mmoles) of Fmoc-Tyr(tBu)-resin were suspended in 25 ml of DMF and after 2 hours they were loaded into the reaction column. Then the cycle of operations described in example 1 was repeated forty-four times, using the suitably activated Fmoc-amino acid in each run, in the order indicated in the sequence reported above. The protected resin-pentatetracontapeptide thus prepared was washed with the usual solvents (see example 1) and dried under vacuum.

Yield: 808 mg.

EXAMPLE 6

Ser-Gln-Gly-Gln-Val-Gln-Pro-Gly-Ala-Arg-Ile-Phe-Ser-Phe-Asp-Gly-Arg-Asp-Val-Leu-Arg-His-Pro-Ala-Trp-Pro-Gln-Lys-Ser-Val-Trp-His-Gly-Ser-Asp-Pro-Ser-Gly-Arg-Arg-Leu-Met-Glu-Ser-Tyr (pentatetracontapeptide III) (SEQ ID NO: 3).

888 mg of protected resin-pentatetracontapeptide were suspended in 141 ml of TFA previously added with 7.5 ml of anisole and 1.5 ml of ethanedithiol. Then the procedure described in example 2 was followed, to obtain 98 mg of pure pentatetracontapeptide III.

[α] −60.5°(c=0.06, water). Mass spectrum: molecular peak (M+1)=5125 Da. Amino acid analysis: Asp=3.04(3); Ser=5.88(6); Glu=4.91(5); Pro=3.93(4); Gly=5.05(5); Ala=2.07(2); Val=2.89(3); Met=0.91(1); Ile=0.95(1); Leu=1.93 (2); Tyr=0.93(1); Phe=2.11(2); Lys=0.97(1); His=1.89(2); Arg=4.84(5); Trp=2.03(2).

EXAMPLE 7

Cys(Trt)-Glu(OtBu)-Thr(tBu)-Trp(Boc)-Arg(Pbf)-Thr(tBu)-Glu(OtBu)-Thr(tBu)-Thr(tBu)-Gly-Ala-Thr(tBu)-Gly-Gln-Ala-Ser(tBu)-Ser(tBu)-Leu-Leu-Ser(tBu)-Gly-Arg(Pbf)-Leu-Leu-Glu(OtBu)-Gln-Lys(Boc)-Ala-Ala-Ser(tBu)-Cys(Trt)-His(Trt)-Asn-Ser(tBu)-Tyr(tBu)-Ile-Val-Leu-Cys(tBu)-Ile-Glu(OtBu)-Asn-Ser(tBu)-Phe-Met-Thr(tBu)-Ser(tBu)-Phe-Ser(tBu)-Lys(Boc)-resin (SEQ ID NO: 8).

770 mg (0.1 mmoles) of Fmoc-Lys(Boc)-resin were suspended in 30 ml of DMF and after 2 hours loaded into the reaction column. All the other Fmoc-amino acids were assembled in the order indicated in the sequence reported above, using for each of them the operative cycle reported in example 1. 1340 mg of protected resin-pentacontapeptide were obtained.

EXAMPLE 8

Cys-Glu-Thr-Arg-Thr-Glu-Thr-Thr-Gly-Ala-Thr-Gly-Gln-Ala-Ser-Ser-Leu-Leu-Ser-Gly-Arg-Leu-Leu-Glu-Gln-Lys-Ala-Ala-Ser-Cys-His-Asn-Ser-Tyr-Ile-Val-Leu-Cys(tBu)-Ile-Glu-Asn-Ser-Phe-Met-Thr-Ser-Phe-Ser-Lys (pentacontapeptide IV) (SEQ ID NO: 4).

1340 mg of protected resin-pentacontapeptide were treated with a mixture of 188 ml of TFA, 10 ml of anisole and 2 ml of ethanedithiol. Then the cycle of operations described in example 2 was repeated to obtain 342 mg of pentacontapeptide IV.

335 mg of said peptide were dissolved in 300 ml of 75% methanol and then added drop by drop and under stirring with a solution of 25 mg of iodine in 80 ml of 75% methanol. After reacting the mixture for 3 hours at room temperature, a 10% ascorbic acid solution was added until complete decolourization of iodine. Methanol was thoroughly evaporated off under vacuum and the remaining aqueous solution was freeze-dried. The resulting crude peptide was finally purified by semipreparative HPLC, in the conditions described above. 67 mg of pure pentacontapeptide were obtained.

[α] −14.5°(c=0.2, acetic acid 80%). Mass spectrum: molecular peak (M+1)=5502 Da. Amino acid analysis: Asp=2.03(2); Thr=5.87(6); Ser=7.79(8); Glu=6.03(6); Gly=2.87 (3); Ala=4.04(4); Cys=2.86(3); Val=0.97(1); Met=0.89(1); Ile=2.11(2); Leu=4.92(5); Tyr=1.05(1); Phe=2.11(2); Lys=1.93(2); His=1.04(1); Arg=1.87(2); Trp=0.93(1).

The biological activity of the polypeptides of the invention is illustrated in the following Experimental Section.

Pharmacological Assays

Cell Lines and Culture Conditions

The coronary venular endothelial cells (CVEC) were isolated and cultured as previously described (8).

BALB/c mouse aortic endothelial 22106 cells (MAE) were grown as previously described (9).

Bovine aortic smooth muscle cells (BASM) were isolated and grown as previously described (10).

The fibroblast NIH-3T3 and A-431 cells were obtained from American Type Culture Collection (Rockville, Md.) and grown accordingly with manufacturer instructions.

Cytotoxicity

The cytotoxic effect of peptides was studied by trypan blue exclusion (11).

Migration Assay

Cell migration was assessed in 48-well microchemotaxis chambers (NeuroProbe, Biomap, Milan, Italy) on a polycarbonate filter as previously described (12,13).

Gelatin Zymography

Conditioned media from cells exposed for 24 hr to test compounds were subjected to electrophoresis in SDS-PAGE containing 1 mg/ml gelatin as previously described (14). Gelatinase activity was evaluated by quantitative densitometry of the bands.

Proliferation Studies

Cell proliferation was quantified by total cell number as reported (12,13).

Vascular Sprouting In Vitro

Vascular sprouting from mouse aorta rings was assessed in three-dimensional fibrin gels preparations according to the method described by Brown et al (15), with minor modifications. Quantitative evaluation of newly formed structures was carried out at day 3. The area covered by vascular sprouts was quantified in microscopic units (0.21 mm$^2$).

Angiogenesis In Vivo: Rabbit Cornea Assay

Angiogenesis was studied in the cornea of albino rabbits as previously described (11,12,13).

Results

Cytotoxic Effects on Cultured Cells

Endothelial and non endothelial cell lines and among the latter tumor and non-neoplastic stromal cell lines were used. To assess cytotoxicity all cell suspensions were exposed for 30 min at 37° C. to 10 and 300 ng/ml of the peptides. No significant increase of cell death was detected with the trypan blue-exclusion test.

Effect on Endothelial Cell Migration

Cell migration was assessed in 48-well micro-chemotaxis chambers. All the peptides inhibited the migration induced by FGF-2 and VEGF and exhibited different potency according to the concentration. An example of the inhibitory effect exerted by the fragments at the concentration of 10 ng/ml is shown in FIG. 1A-B. Surprisingly, the endostatin peptides could induce endothelial cell migration in non stimulated cells.

Effect on Metalloprotease Activity

No modification of basal and stimulated metalloprotease activity was detected by gelatin zymography in the conditioned medium of endothelial cells treated with the endostatin peptides.

Effect on Cell Proliferation

Cell proliferation was quantified by counting the total number of cells after 48 hr treatment. Endothelial cells isolated from postcapillary venules were used to test the effect on angiogenesis. The endostatin fragments did not inhibit proliferation when tested at concentration between 1 and 1000 ng/ml, whereas the end fragments were able to inhibit cell growth induced by FGF-2 and VEGF when tested at concentrations ranging between 10 and 1000 ng/ml. The effect was more pronounced on FGF-2-induced growth. Interestingly, Fragment IV was the most potent in inhibiting endothelial cell proliferation (FIG. 1C-D). Similar effects were obtained on all the endothelial cell lines tested (FIG. 1E).

The selectivity of the peptides for endothelium was assessed on non-endothelial cell lines of vascular and non-vascular origin and on tumor cells from various sources (murine and human). Non-endothelial cells were not affected by the endostatin peptides (FIG. 2).

Effects on In Vitro Angiogenesis

The formation of capillary-like structures in vascular rings cultured in 3D fibrin gels was used to test angiogenesis in vitro. Fragment I and IV inhibited the spontaneous growth of capillaries and the one induced by FGF-2 and VEGF. As an example the effect of 100 ng/ml concentration of either fragment is shown (FIG. 3A).

Effect on In Vivo Angiogenesis

The angiostatic effect of endostatin fragments in vivo was assessed in the avascular rabbit cornea assay. VEGF induced an efficient and persistent neovascularization of the corneal stroma. When VEGF was tested in the presence of endostatin fragments a consistent inhibition of angiogenesis was produced. An example of the effect exerted by Fragments I and IV at 200 ng/pellet is shown in FIG. 3B. When tested as single agents the peptides did not exhibit major pro-inflammatory properties.

Comparison with Recombinant Full Length Endostatin

The effect of endotstatin fragments was compared to recombinant human full length endostatin produced by Dr. M. Rehn (La Jolla Cancer Research Center, La Jolla, USA).

Surprisingly, endostatin peptides resulted more efficient than full length endostain in inhibiting angiogenesis induced by VEGF (FIG. 3B).

C–E: Effect of endostatin fragments on endothelial cell proliferation. Endothelial cell (C,D: CVEC; E, MAE) proliferation was stimulated with FGF-2 and VEGF (20 ng/ml each). Data are expressed as number of cells counted/well after 48 hr incubation with test substances. Numbers are means±SEM of 6 and 2 experiments run in triplicate for CVEC and ME, respectively.

*$P<0.05$ vs FGF-2 and VEGF alone. (Student's t test)

Figure 1:
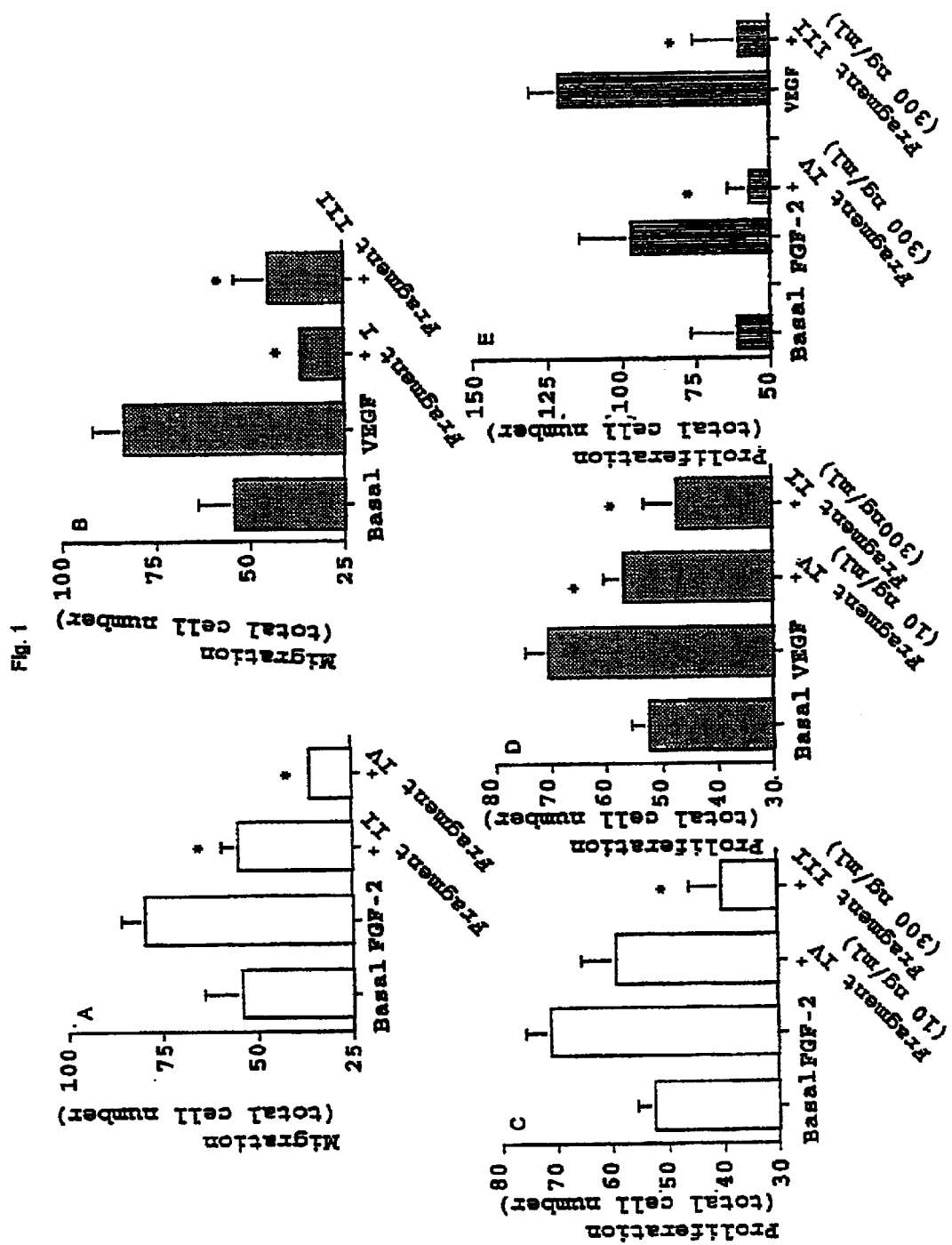
FIG. 1: Effect of endostatin fragments on endothelial cell migration (A,B) and proliferation (C–E). A,B: Fragments (10 ng/ml) were added together to the angiogenic factors (20 ng/ml each) in the lower compartments of the NeuroProbe microchemotaxis chamber. Incubation was carried out for 4 hr and migrated cells were microscopically counted in a blind manner. Data are expressed as total cell number counted/well. Numbers are means±SEM of 6 experiments run in triplicate.
Figure 2:
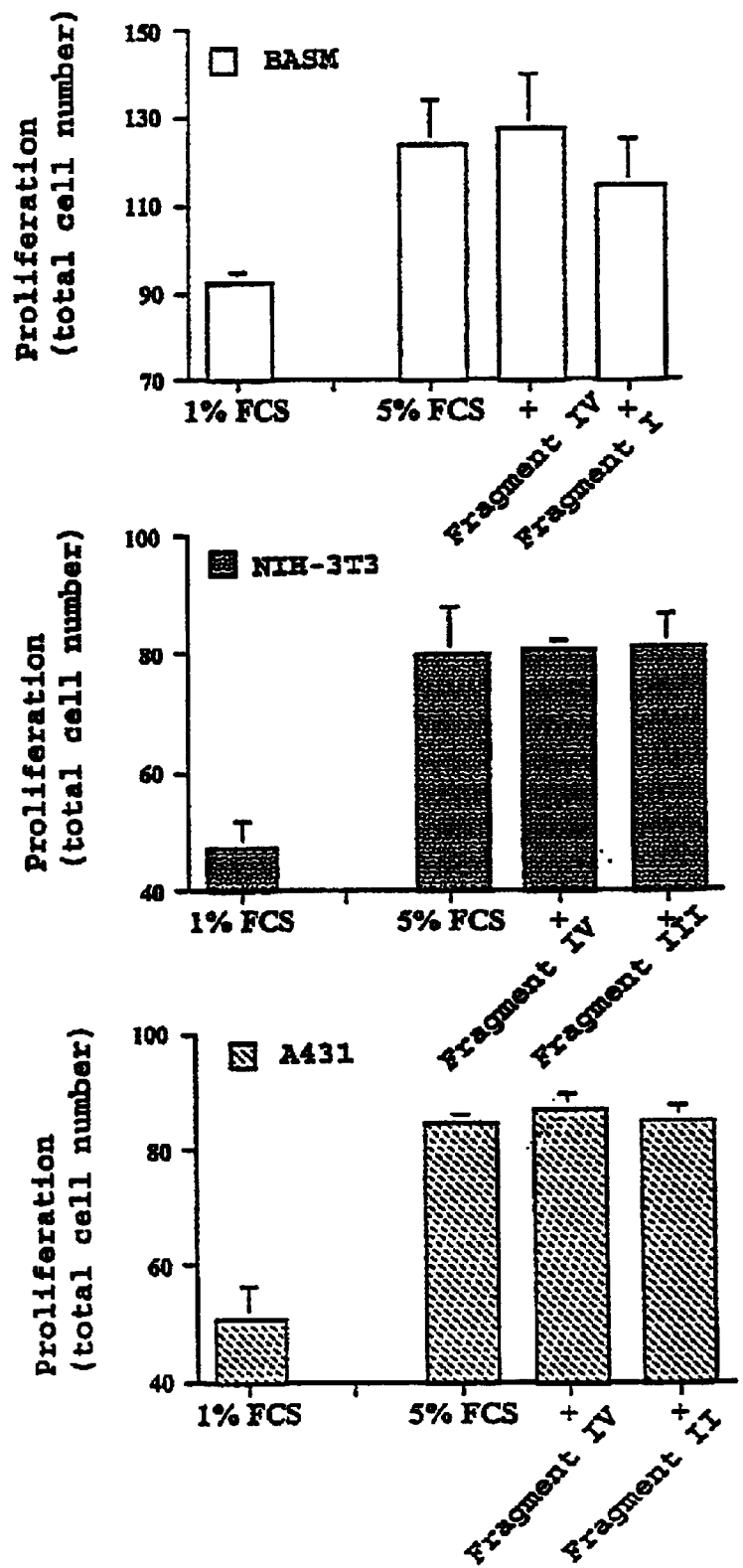

FIG. 2: Effect of endostatin fragments on non-endothelial cell lines. Proliferation of bovine aortic smooth muscle cells (BASM, upper panel), murine fibroblasts (NH-3T3, middle panel) and tumor cells (A431, lower panel) was evaluated as described in FIG. 2. Cell growth was stimulated with 5% FCS. Fragments were evaluated at the concentration of 300 ng/ml. Numbers are means±SEM of 2 experiments run in triplicate.

Figure 3:
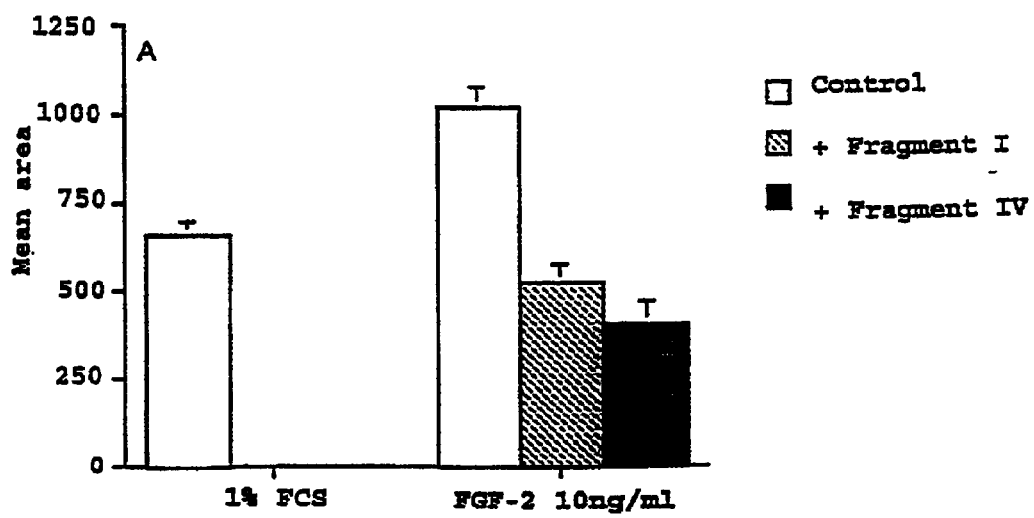
Figure 3:
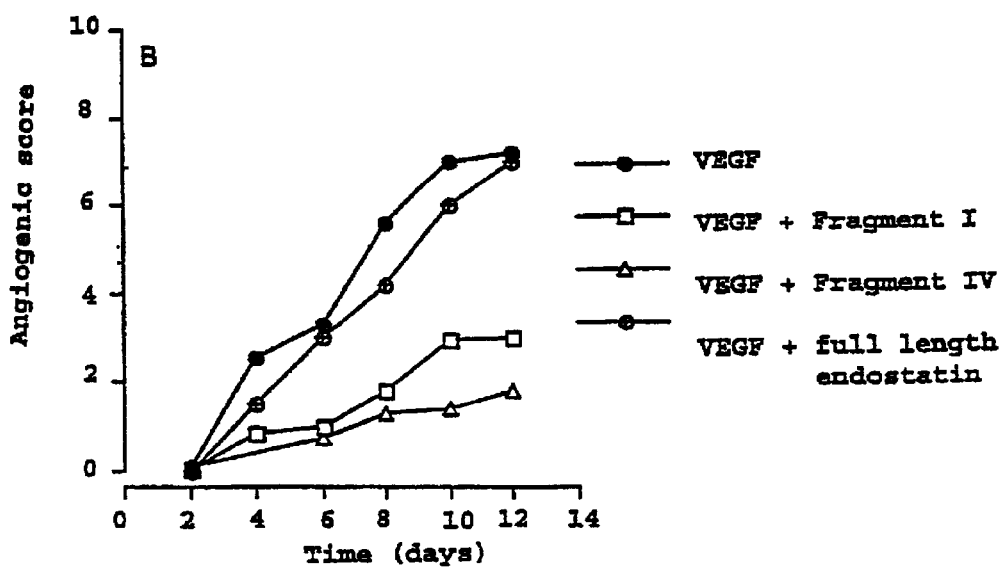

FIG. 3: Effect of endostatin fragments on angiogenesis in vitro (A) and in vivo (B). A. In vitro vessel sprouting from rings of mouse aortas was induced by FGF-2 (10 ng/ml). Fragments I and IV were used at 100 µg/ml. Data are reported as mean area occupied by tubules-like structures after 3 days from stimulation. Numbers are means of one representative experiment out of two run in triplicate.

B. Effect of endostatin fragments on in vivo angiogenesis in the avascular rabbit cornea model. Endostatin fragments (200 ng) or full length endostatin (3 ug) were incorporated in the same pellet preparation together with VEGF (200 ng). The angiogenic activity was compared to VEGF alone. Data are reported as angiogenic score during time (days) and are the means of 5 implants.

CONCLUSIONS

The peptides studied exert a potent and direct antiangiogenic effect in vitro and in vivo. The peptides act by selectively inhibiting endothelial cell growth and migration induced by angiogenic factors. Endostatin peptides resulted more efficient than full length endostain in inhibiting in viva angiogenesis.

REFERENCES

1. Folkman J. Angiogenesis in cancer, vascular, rheumatoid and other disease. Nature Medicine 1995; 1: 27–31.
2. Hanahan D and Folkman J. Patterns and emerging mechanism of the angiogenic switch during tumorigenesis. Cell 1996; 86: 353–364.
3. Folkman J. Clinical applications of research on angiogenesis. N Engl J Med 1995; 333: 1757–1763.2.
4. Risau W. Mechanism of angiogenesis. Nature 1997; 386: 671–674.
5. O'Really M S et al. Endostatin: an endogenous inhibitor of angiogenesis and tumor growth. Cell 1997; 88: 277–285.
6. Boehm T, et al. Anti angiogenic therapy of experimental cancer does not induce acquired drug resistance. Nature 1997; 390: 404–407.
7. Taddei L, et al. Inhibitory effect of full-length human endostatin on in vitro angiogenesis. Biochem Biophys Res Commun 1999; 263:340–345.
8. Schelling M E, et al. Venular endothelial cells from bovine heart. Am J Physiol 1988, 254, H1211–H1217.
9. Gualandris A, et al. Basic fibroblast growth factor overexpression in mouse endothelial cells: an autocrine model of angiogenesis and angioproliferative diseases. Cell Growth Differ, 1996, 7: 147–160.
10. Catalioto R M, et al. Roel of calcium in angiotensin II-induced prostaglandin release and DNA synthesis in rat vascular smooth muscle cells. J. cardiuovascular Pahramcol. 1996, 27: 195–200.
11. Presta M, et al. Purine analog 6-methylmercaptopurine ribose inhibits early and late phases of the angiogenesis process. Cancer Res. 1999, 59(10): 2417–2424.
12. Ziche M, et al. Nitric oxide mediates angiogenesis in vivo and endothelial cell growth and migration in vitro promoted by substance P. J Clin Invest 1994; 94, 2036–2044.
13. Ziche M, et al. Nitric oxide-synthase lies downstream of vascular endothelial growth factor but not basic fibroblast growth factor induced angiogenesis. J. Clin. Invest. 1997; 99, 2625–2634.
14. Qian X, et al. Thrombospondin-1 modulates angiogenesis in vitro by up-regulation of matrix metalloproteinase-9 in endothelial cells. Exp Cell Res. 1997, 235, 403–412.
15. Brown K J, et al. A novel in vitro assay for human angiogenesis, Lab. invest. 1996, 75(4):539–555.
16. J. Folkman, O. C. Haudenschild and B. R. Zetter, Proc. Natl. Acad. Sci. USA 76, 5217, 1979. M. Ziche, L. Morbidelli, S. Donnini and F. Ledda, J. Cardiovasc. Pharmacol., 26 (Suppl. 3), S284, 1995.
17. A. Dryland and R. C. Sheppard, J. Chem. Soc., Perkin 1, 125, 1986.
18. E. Bayer, Angew. Chem., 103, 117, 1991.

What is claimed is:

1. A polypeptide comprising homologous to that of endostatin and having antiangiogenic activity, the polypeptide which is pentacontapeptide IV having the sequence Cys-Glu-Thr-Trp-Arg-Thr-Glu-Thr-Thr-Gly-Ala-Thr-Gly-Gln-Ala-Ser-Ser-Leu-Ser-Gly-Arg-Leu-Leu-Glu-Gln-Lys-Ala-Ala-Ser-Cys-His-Asn-Ser-Tyr-Ile-Val-Leu-Cys(tBu)-Ile-Glu-Asn-Ser-Phe-Met-Thr-Ser-Phe-Ser-Lys (SEQ ID NO:4).

2. A process for the preparation of the polypeptide as claimed in claim 1 comprising preparing said polypeptide by solid phase synthesis.

3. The process as claimed in claim 2, characterized in that said synthesis is completed by an automatic synthesizer.

4. A pharmaceutical formulation with antiangiogenic activity, consisting of the polypeptide as claimed in claim 1.

5. A pharmaceutical formulation with antiangiogenic activity, comprising as an active ingredient the polypeptide according to claim 1.

6. A method for the preparation of medicaments with antiangiogenic activity comprising the step of adding an effective amount of the polypeptide claimed in claim 1 to an excipient.

7. A method for inhibiting angiogenesis activity of an angiogenesis dependent tumor in a subject, comprising administering to said subject an effective amount of the polypeptide according to claim 1.

* * * * *